United States Patent [19]

Kushnerick et al.

[11] Patent Number: 4,827,069

[45] Date of Patent: * May 2, 1989

[54] UPGRADING LIGHT OLEFIN FUEL GAS AND CATALYTIC REFORMATE IN A TURBULENT FLUIDIZED BED CATALYST REACTOR

[75] Inventors: J. Douglas Kushnerick, Boothwyn, Pa.; Mohsen N. Harandi, Lawrenceville; Hartley Owen, Belle Mead, both of N.J.

[73] Assignee: Mobil Oil Corporation, New York, N.Y.

[*] Notice: The portion of the term of this patent subsequent to May 24, 2005 has been disclaimed.

[21] Appl. No.: 157,830

[22] Filed: Feb. 19, 1988

[51] Int. Cl.⁴ .............................................. C07C 12/02
[52] U.S. Cl. .................................... 585/415; 585/417; 585/467; 585/533
[58] Field of Search ................ 585/415, 417, 467, 533

[56] References Cited

U.S. PATENT DOCUMENTS

| | | | |
|---|---|---|---|
| 3,751,506 | 8/1973 | Burress | 585/467 |
| 3,755,483 | 8/1973 | Burress | 585/467 |
| 3,827,968 | 1/1973 | Givens et al. | 208/49 |
| 4,016,218 | 4/1977 | Haag et al. | 585/467 |
| 4,140,622 | 2/1979 | Herout et al. | 208/93 |
| 4,209,383 | 6/1980 | Herout et al. | 208/93 |
| 4,393,262 | 7/1983 | Kaeding | 585/467 |
| 4,497,968 | 2/1985 | Wright et al. | 585/304 |
| 4,542,251 | 9/1985 | Miller | 585/533 |
| 4,746,762 | 5/1988 | Avidan et al. | 585/415 |

Primary Examiner—Curtis R. Davis
Attorney, Agent, or Firm—Alexander J. McKillop; Charles J. Speciale; L. G. Wise

[57] ABSTRACT

A fluidized bed catalytic process for conversion of light olefinic gas feedstock containing ethene and propene to produce $C_5^+$ hydrocarbons and for the conversion of catalytic reformate feedstock to produce $C_7$-$C_{11}$ aromatic hydrocarbons, comprising a maintaining a fluidized bed of zeolite catalyst particles in a turbulent reactor bed at a temperature of about 600° to 750° F. (316° to 399° C.) and pressure of about 100 to 250 psig (790 to 825 kPa. The catalyst has an apparent particle density of about 0.9 to 1.6 g/cm³ and a size range of about 1 to 150 microns, and average catalyst particle size of about 20 to 100 microns containing about 10 to 25 weight percent of fine particles having a particle size less than 32 microns. The feed vapor is passed upwardly through the fluidized catalyst bed under turbulent flow conditions; turbulent fluidized bed conditions are maintained through the reactor bed between transition velocity and transport velocity at a superficial fluid velocity of about 0.3 to 2 meters per second; and hydrocarbon product is recovered containing $C_5^+$ hydrocarbons and $C_7$ to $C_{11}$ aromatic hydrocarbons.

13 Claims, 1 Drawing Sheet

FIG.
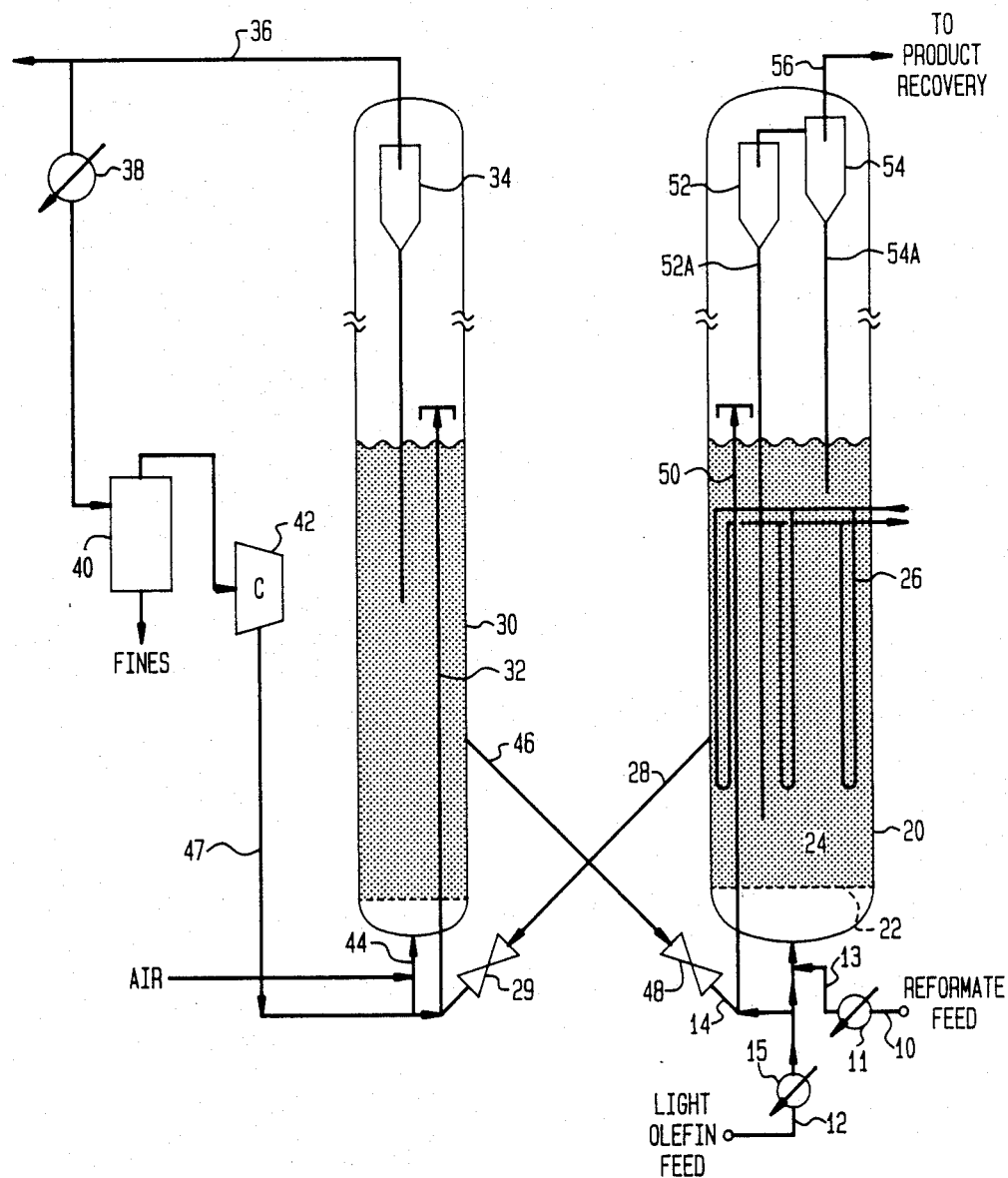

UPGRADING LIGHT OLEFIN FUEL GAS AND CATALYTIC REFORMATE IN A TURBULENT FLUIDIZED BED CATALYST REACTOR

CROSS-REFERENCE TO RELATED APPLICATIONS

This application is related to Avidan U.S. Ser. No. 006,407 filed Jan. 23, 1987 and application Ser. No. 157,831 filed concurrently, both of which are assigned to applicant's assignee and are incorporated herein by reference thereto.

FIELD OF THE INVENTION

The present invention relates to a petroleum refining process for the production of gasoline product. The present invention more specifically relates to the production of gasoline by contacting a $C_4^-$ fuel gas containing ethene and propene with a catalytic reformate containing $C_6$ to $C_8$ aromatics over a fluidized bed of zeolite catalyst to convert the fuel gas to $C_5^+$ hydrocarbon gasoline and to convert the $C_6$ to $C_8$ aromatics to lower alkyl aromatic hydrocarbon gasoline. The process includes the catalytic reforming of naptha to obtain the catalytic reformate feed and the catalytic cracking of hydrocarbons to obtain the $C_4^-$ fuel gas feed to the fluidized bed zeolite catalyst conversion zone.

BACKGROUND OF THE INVENTION

The fluid catalytic cracking of hydrocarbons in modern refinery operations produce large amounts of $C_4^-$ fuel gas of little or no gasoline product value and the catalytic reforming of hydrocarbons produces large amounts of $C_6$ to $C_8$ aromatic hydrocarbons which though having value as gasoline blending stock is produced in excessive amounts.

This invention relates to a catalytic technique for upgrading light olefin gas to heavier hydrocarbons and to alkylating $C_6$ to $C_8$ aromatics to heavier lower alkyl aromatic hydrocarbons. In particular, it provides a continuous process for reacting olefinic light gas feedstock, containing ethene and propene or other lower alkenes, to produce $C_5^+$ hydrocarbons, such as olefinic liquid fuels and isobutane and other useful products and to at the same time alkylating $C_6$ to $C_8$ aromatics to produce $C_1$ to $C_4$ lower alkyl aromatic hydrocarbons for use as gasoline feedstock. Ethene (ethylene, $C_2H_4$)-containing gases, such as petroleum cracking offgas, and catalytic reformate containing benzene, toluene, xylene and ethyl benzene are useful feedstocks for this process.

Developments in zeolite catalysis and hydrocarbon conversion processes have created interest in utilizing olefinic feedstocks for producing $C_5^+$ gasoline, diesel fuel, etc. In addition to basic chemical reactions promoted by ZSM-5 type zeolite catalysts, a number of discoveries have contributed to the development of new industrial processes. These are safe, environmentally acceptable processes for utilizing feedstocks that contain lower olefins, especially $C_2$-$C_4$ alkenes and for feedstocks containing $C_6$ to $C_8$ aromatic hydrocarbons.

Chen U.S. Pat. No. 3,729,409 discloses improving the yield-octane number of a reformate by contacting the reformate in the presence of hydrogen over a zeolite catalyst. Garwood wet al U.S. Pat. No. 4,150,062 discloses a process for the conversion of $C_2$ to $C_4$ olefins to produce gasoline which comprises contacting the olefins with water over a zeolite catalyst. Haag et al U.S. Pat. No. 4,016,218 and Burress U.S. Pat. No. 3,751,506 disclose processes for the alkylation of benzene with olefins over a ZSM-5 type catalyst. The Herout et al U.S. Pat. No. 4,209,383 discloses the catalytic alkylation of benzene in reformate with $C_3$-$C_4$ olefins to produce gasoline.

Conversion of $C_2$-$C_4$ alkenes and alkanes to produce aromatics-rich liquid hydrocarbon products were found by Cattanach U.S. Pat. No. 3,760,024 and Yan et al U.S. Pat. No. 3,845,150 to be effective processes using the ZSM-5 type zeolite catalysts. In U.S. Pat. Nos. 3,960,978 and 4,021,502, Plank, Rosinski and Givens disclose conversion of $C_2$-$C_5$ olefins, alone or in admixture with paraffinic components, into higher hydrocarbons over crystalline zeolites having controlled acidity. Garwood et al have also contributed to the understanding of catalytic olefin upgrading techniques and improved processes as in U.S. Pat. Nos. 4,211,640 and 4,227,992. The above-identified disclosures are incorporated herein by reference.

It has now been found that contacting a catalytic reformate feed comprising $C_6$ to $C_8$ aromatic hydrocarbons with a light olefin gas feed, comprising ethene and propene, over a zeolite catalyst that the $C_6$ to $C_8$ aromatics in catalytic reformate can be converted to lower alkyl aromatic hydrocarbons while at the same time converting the ethene and propene to $C_5^+$ hydrocarbons, both of which products are suitable for use as gasoline blending stocks.

In accordance with the present invention it has been found that ethene-rich olefinic light gas can be upgraded to liquid hydrocarbons rich in olefinic gasoline, isobutane and aromatics and that catalytic reformate containing $C_6$ to $C_8$ aromatics can be upgraded to lower alkyl aromatic hydrocarbons of higher octane value by catalytic conversion in a turbulent fluidized bed of solid acid zeolite catalyst under reaction conditions in a single pass or with recycle of gas product. This technique is particularly useful for upgrading FCC light gas, which usually contains significant amounts of ethene, propene, $C_2$-$C_4$ paraffins and hydrogen produced in cracking heavy petroleum oils or the like and for upgrading catalytic reformate containing $C_6$ to $C_8$ aromatics and $C_5$ to $C_9$ paraffins. By upgrading the by-product light gas and the catalytic reformate, the gasoline yield of FCC units and catalytic reforming units can be significantly increased. Accordingly, it is a primary object of the present invention to provide a novel technique for upgrading ethene-rich light gas and $C_6$ to $C_8$ rich catalytic reformate.

SUMMARY OF THE INVENTION

An improved process has been found for continuous conversion of ethene-containing and $C_6$ to $C_8$ aromatic hydrocarbon containing feedstocks to heavier hydrocarbon products of higher octane value wherein the feedstock is contacted at elevated temperature with a fluidized bed of zeolite catalyst under conversion conditions. The improvement comprises maintaining the fluidized catalyst bed in a vertical reactor column having a turbulent reaction zone by passing feedstock gas upwardly through the reaction zone at a velocity greater than dense bed transition velocity in a turbulent regime and less than transport velocity for the average catalyst particle; and withdrawing a portion of coked catalyst from the reaction zone, oxidatively regenerating the withdrawn catalyst and returning regenerated catalyst to the reaction zone at a rate to control catalyst activity.

In accordance with the present invention in the same reaction zone an ethene-rich olefinic light gas can be upgraded to liquid hydrocarbons rich in olefinic gasoline and a catalytic reformate rich in $C_6$ to $C_8$ aromatics can be upgraded to lower alkyl aromatic hydrocarbons of higher octane value by catalytic conversion in the turbulent regime of a fluidized bed of solid acid zeolite catalyst in a single pass or with recycle of light gas product.

The present invention is particularly useful for upgrading FCC light gas, which usually contains significant amounts of ethene or ethene and propene and for upgrading catalytic reformate which usually contains significant amounts of benzene, toluene, xylene and ethyl benzene.

Advantageously, the fluidized bed technique can employ a single pass ethene or ethene and propene conversion of at least 80% to provide high octane $C_5+$ gasoline range hydrocarbon product in good yield and $C_6$ to $C_8$ aromatic hydrocarbon conversion of at least 5% to provide higher octane $C_7$ to $C_{11}$ aromaic hydrocarbon gasoline range product in good yield. A mixture of alkenes, alkanes and $C_6$ to $C_8$ aromatics can be converted without significant recycle and/or diluent to provide high octane gasoline range hydrocarbon product in good yield. However, recycle of $C_4-$ gas can be used to increase yields further and lower catalyst make-up requirements.

An object of the present invention to provide a novel economical process for catalytically converting a hydrocarbon feed stream containing light olefins, including ethene and propene, and a hydrocarbon stream containing $C_6$ to $C_8$ aromatic hydrocarbons, by contacting the two feed streams together and in the turbulent regime of a fluidized bed of zeolite catalyst to convert the light olefin hydrocarbon feed to $C_5+$ hydrocarbon, e.g. $C_5+$ aliphatic hydrocarbon, and to convert the $C_6$ to $C_8$ aromatic hydrocarbons to $C_7$ to $C_{11}$ aromatic hydrocarbon gasoline products.

BRIEF DESCRIPTION OF THE DRAWING

The FIGURE of the drawing illustrates an embodiment of the invention in which the reaction is carried out in the tubulent zone of a fluidized bed and the regeneration and recycle of the catalyst.

DESCRIPTION OF PREFERRED EMBODIMENTS

Description of the Process

The present invention utilizes conventional petroleum refining steps including fractionation, hydrotreating, catalytic reforming and fluidized catalytic cracking and a novel zeolite catalyst process to upgrade fuel gas and reformate process streams.

In accordance with the present invention a gasoline boiling range product is produced from a fuel gas stream from the fluidized catalytic process step and a reformate stream from the catalytic reforming step.

The zeolite catalyst reaction zone is operated under conditions such that ethene or ethene and propene in a fuel gas feedstream are converted to $C_5+$ olefinic gasoline product and ethene or ethene and propene in the fuel gas feedstream in addition react with the $C_6$ to $C_8$ aromatics in a reformate feedstream to produce $C_7$ to $C_{11}$ alkyl aromatic hydrocarbons such as toluene, xylene, ethyl benzene, methyl ethyl benzene, diethyl benzene and propyl benzene.

The effluent stream from the zeolite reaction zone is passed into a separator in which a $C_6-$ hydrocarbon stream is removed overhead and fed to an absorber in which the $C_3+$ hydrocarbons are absorbed and removed. The remaining $C_3-$ hydrocarbons are taken overhead and can be recycled to the zeolite catalyst reaction zone. The bottoms from the separator contain $C_7$ to $C_{11}$ aromatic hydrocarbons and $C_5+$ hydrocarbons and is fed to a debutanizer from which an overhead $C_4-$ gas stream is removed. A portion of the $C_4-$ stream can be recycled to the zeolite catalyst reaction zone. The debutanized gasoline product is removed as a bottoms product and is fed to the gasoline product pool.

Description of Catalysts

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, B or Fe, within the zeolitic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 Argauer et al, incorporated by reference.

The zeolite catalysts preferred for use herein include the medium pore (i.e., about 5–7A) shape-selective crystalline aluminosilicate zeolites having a silica-to-alumina ratio of at least 12, a constraint index of about 1 to 12 and acid cracking activity of about 1–200. In the fluidized bed reactor the coked catalyst may have an apparent activity (alpha value) of about 1 to 80 under the process conditions to achieve the required degree of reaction severity. Representative of the ZSM-5 type zeolites are ZSM-5, ZSM-11, ZSM-12, ZSM-22, ZSM-23, ZSM-35 and ZSM-38. ZSM-5 is disclosed in U.S. Pat. No. 3,702,886 and U.S. Pat. No. Re. 29,948. The ZSM-5 and ZSM-12 catalyst are preferred. Other suitable zeolites are disclosed in U.S. Pat. Nos. 3,709,979, 3,832,449, 4,076,979, 3,832,449, 4,076,842, 4,016,245 and 4,046,839, 4,414,423, 4,417,086, 54,517,396 and 4,542,251. The disclosures of these patents are incorporated herein by reference. While suitable zeolites having a coordinated metal oxide to silica molar ratio of 20:1 to 200:1 or higher may be used, it is advantageous to employ a standard ZSM-5 having a silica alumina molar ratio of about 25:1 to 70:1, suitably modified. A typical zeolite catalyst component having Bronsted acid sites may consist essentially of aluminosilicate ZSM-5 zeolite with 5 to 95 wt.% silica and/or alumina binder.

Certain of the ZSM-5 type medium pore shape selective catalysts are sometimes known as pentasils. In addition to the preferred aluminosilicates, the borosilicate, ferrosilicate and "silicalite" materials may be employed. It is advantageous to employ a standard ZSM-5 having a silica:alumina molar ratio of 25:1 to 70:1 with an apparent alpha value of 1–80 to convert 60 to 100 percent, preferably at least 70%, of the olefins in the feedstock and to convert 1 to 50% preferably at least 5% of the $C_6$ to $C_8$ aromatics in the feedstock.

ZSM-5 type pentasil zeolites are particularly useful in the process because of their regenerability, long life and stability under the extreme conditions of operation.

Usually the zeolite crystals have a crystal size from about 0.01 to over 2 microns or more, with 0.02–1 micron being preferred. In order to obtain the desired particle size for fluidization in the turbulent regime, the zeolite catalyst crystals are bound with a suitable inorganic oxide, such as silica, alumina, etc. to provide a zeolite concentration of about 5 to 95 wt.%. A preferred catalyst comprises 25 to 35% H-ZSM-5 catalyst contained within a silica-alumina matrix binder and having a fresh alpha value of less than 80.

Particle size distribution can be a significant factor in achieving overall homogeneity in turbulent regime fluidization. It is desired to operate the process with particles that will mix well throughout the bed. Large particles having a particle size greater than 250 microns should be avoided, and it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt.% of the total catalyst in the reaction zone in the size range less than 32 microns. This class of fluidizable particles is classified as Geldart Group A. Accordingly, the turbulent fluidization regime is controlled to assure operation between the transition velocity and transport velocity. Fluidization conditions are substantially different from those found in non-turbulent dense beds or transport beds.

Hydrocarbon Feed Streams To Turbulent Regime Fluidized Bed Zeolite Catalyst Reaction Zone

(A) Light Olefin Gas

The preferred light olefin gas feedstock contains $C_2$ to $C_4$ alkenes (mono-olefins) including at least 2 moles % ethene, wherein the total $C_2$–$C_3$ alkenes are in the range of 10 to 40 wt.%. Non-deleterious components, such as methane, $C_3$–$C_4$ paraffins and inert gases, may be present. Some of the paraffins will be converted to $C_4^+$ hydrocarbons depending on the reaction conditions and catalyst employed. A particularly useful feedstock is a light gas by-product of FCC gas oil cracking units containing typically 10–40 mol% $C_2$–$C_3$ olefins and 5–35 mol% $H_2$ with varying amounts of $C_1$–$C_3$ paraffins and inert gas, such as $N_2$. The feedstock can contain primarily ethene or ethene and propene.

The light olefine feed gas is described in more detail in the Table 1 below.

TABLE 1

|  | Broad | Intermediate | Preferred |
|---|---|---|---|
| Mole % | | | |
| $H_2$ | 0 to 50 | 5 to 50 | 5 to 30 |
| Ethene | 1 to 90 | 5 to 40 | 5 to 25 |
| Propene | 0 to 90 | 1 to 40 | 1 to 25 |
| Weight % | | | |
| $H_2$ | 0 to 10 | 1 to 10 | 1 to 4 |
| Ethene | 1 to 90 | 8 to 50 | 8 to 35 |
| Propene | 0 to 90 | 3 to 50 | 3 to 40 |
| Ethene/Propene | 1 to 90 | 5 to 80 | 5 to 60 |

Catalytic Reformate

The catalytic reformate feedstock contains $C_6$ to $C_8$ aromatic hydrocarbons and $C_5$ to $C_7$ paraffinic hydrocarbons. The $C_6$ to $C_8$ aromatic hydrocarbons include benzene, toluene, xylene and ethyl benzene. The xylene and ethyl benzene are herein considered together as $C_8$ aromatic hydrocarbon. Though the catalytic reformate is a preferred feedstock, hydrocarbon process streams containing essentially the same hydrocarbon components can also be used.

The catalytic reformate feedstock is described in more detail below in Table 2.

TABLE 2

|  | Broad | Intermediate | Preferred |
|---|---|---|---|
| Specific Gravity | 0.72 to 0.88 | 0.76 to 0.88 | 0.76 to 0.83 |
| Boiling Range, °F. | 60 to 400 | 60 to 400 | 80 to 390 |
| Mole % | | | |
| Benzene | 1.0 to 60 | 2 to 40 | 2 to 20 |
| Toluene | 2.0 to 60 | 10 to 40 | 10 to 35 |
| $C_8$ Aromatic[1] | 4.0 to 60 | 4 to 50 | 4 to 40 |
| Weight % | | | |
| Benzene | 1.0 to 60 | 2 to 40 | 2 to 20 |
| Toluene | 2.0 to 60 | 10 to 40 | 10 to 35 |
| $C_8$ Aromatic[1] | 4.0 to 60 | 4 to 50 | 4 to 40 |
| $C_6$ to $C_8$ Aromatics | 5 to 100 | 10 to 95 | 15 to 95 |

[1]Xylene and ethyl benzene component.

Hydrocarbon Products

The contacting of the light olefin gas feed with the catalytic reformate feed over the zeolite catalyst in accordance with the present invention produces the following products.

The ethene and propene components of the light olefin gas feed react to produce primarily $C_5$ to $C_9$ olefinic, $C_5$ to $C_9$ paraffinic and $C_6$ to $C_8$ aromatic gasoline products which have a higher product value than the ethene and propene in the feed. The principle product is the $C_5$ to $C_9$ olefinic gasoline product, i.e. the $C_5^+$ olefinic hydrocarbons.

The ethene and propene components of the light olefin gas feed in addition react with the $C_6$ to $C_8$ aromatics in the catalytic reformate feed to produce primarily $C_7$ to $C_{11}$ aromatics which may themselves rearrange and transalkylate over the zeolite catalyst.

The $C_7$ to $C_{11}$ aromatic hydrocarbon product obtained includes $C_1$ to $C_4$ lower alkyl substituted aromatic hydrocarbons such as methyl, ethyl, propyl and butyl benzene compounds. The $C_7$ to $C_{11}$ aromatic hydrocarbon product contains one or more of the foregoing lower alkyl substituents, providing however that the total numbers of carbon atoms in the subtituents does not exceed 5. Typical $C_7$ to $C_{11}$ aromatic hydrocarbons include toluene, xylene, ethyl benzene, methyl ethyl benzene, propyl benzene, methyl propyl benzene, butyl benzene, methyl butyl benzene and diethyl benzene.

The incorporation of the $C_5^+$ hydrocarbon component, e.g. the $C_5^+$ olefinic hydrocarbons, into the $C_7$–$C_{11}$ aromatic hydrocarbon component enriches the overal octane quality of the gasoline product obtained.

The zeolite catalyst process conditions of temperature and pressure in the turbulent regime of the fluidized bed are closely controlled to minimize cracking of $C_3$ to $C_6$ paraffin hydrocarbons in the feed and is an important feature of the present invention.

Unreacted ethene and propane, and butene formed in the reaction can be recycled to the zeolite catalyst reactor.

The ethene and propene in the light olefin feed are converted in an amount of 20 to 100, preferably 60 to 100 and more preferably 80 to 100 wt.% of the feed.

The $C_6$ to $C_8$ aromatics in the catalytic reformate feed, including benzene, toluene and $C_8$ aromatics, are converted in an amount of 5 to 60, preferably 5 to 50 and more preferably 8 to 35 wt.% of the feed.

Process Conditions

The process of the present invention using a ZSM-5 type zeolite catalyst is carried out at temperatures of 400° to 800° F. (204° to 427° C.), e.g. 500° to 800° F. (260° to 427° C.), preferably 500° to 750° F. (260° to 399° C.) and more preferably 600° to 750° F. (316° to 399° C.).

The pressure at which the reaction is carried out is an important parameter of the invention. The process can be carried out at pressures of 50 to 500 psig (445 to 3550 kPa), preferably 100 to 400 psig (790 to 2860 kPa) and more preferably 100–250 psig (790 to 1825 kPa).

The weight hourly space velocity (WHSV) of the light olefin feed and the catalytic reformate feed are also important parameters of the process.

The principal reactants in the process are the ethene or ethene and propene constituents of the light olefin gas and the $C_6$ to $C_8$ aromatic constituent of the catalytic reformate and the WHSV are given in terms of these components.

The ethene and propene WHSV can be 0.1 to 5.0, preferably 0.1 to 2 and more preferably 0.5 to 1.5.

The $C_6$ to $C_8$ aromatics WHSV can be 0.01 to 6.0, preferably 0.1 to 4.0 and more preferably 0.1 to 2.0.

The $C_5+$ hydrocarbon production and alkyl aromatic production is promoted by those zeolite catalysts having a high concentration of Bronsted acid reaction sites. Accordingly, an important criterion is selecting and maintaining catalyst inventory to provide either fresh catalyst having acid activity or by controlling catalyst deactivation and regeneration rates to provide an apparent average alpha value of about 1 to 80.

THE REACTOR

The use of the turbulent regime fluidized bed catalyst process permits the conversion system to be operated at low pressure drop. An important advantage of the process is the close temperature control that is made possible by turbulent regime operation, wherein the uniformity of conversion temperature can be maintained within close tolerances, often less than 25° C. Except for a small zone adjacent the bottom gas inlet, the midpoint measurement is representative of the entire bed, due to the thorough mixing achieved.

In a typical process, the ethene-rich $C_2+$ olefinc feedstock and $C_6$ to $C_8$ rich feedstock are converted in a catalytic reactor under 600° to 750° F. (260° to 399° C.) temperature and moderate pressure 100 to 250 psig (i.e. 790 to 1825 kPa) to produce a predominantly liquid product consisting essentially of $C_5+$ aliphatic hydrocarbons rich in gasoline-range olefins and $C_7$ to $C_{11}$ alkyl aromatic hydrocarbons.

Refering to the FIGURE of the drawing, a pressurized feed gas rich in $C_2$–$C_3$ olefins is fed through line 12 and heated in heat exchanger 15 and then fed to line 13. A pressurized reformate feed rich in $C_6$–$C_8$ aromatic hydrocarbons is fed through line 10 and heated in heat exchanger 11 and then fed to line 13 wherein it is contacted and mixed with heated olefin feed gas. A major portion of the olefin feed gas is mixed in line 13 with the reformate feed and fed through line 13 to the bottom inlet of reactor vessel 20 for distribution through grid plate 22 into fluidization zone 24. Here the mixed olefin and $C_6$ to $C_8$ aromatic hydrocarbon feed contact the turbulent bed of finely divided catalyst particles. The remainder of the heated olefin feed gas is fed through line 14 to catalyst return riser conduit 50 in which it functions as a lift gas for the regenerated catalyst.

The reaction heat can be partially or completely removed by using cold or only partically preheated olefin feed gas and catalytic reformate feed. Baffles may be added to the reactor vessel to control radial and axial mixing. Heat released from the reaction can be controlled by adjusting feed temperature in a known manner.

Catalyst outlet means 28 is provided for withdrawing catalyst from bed 24 and passed for catalyst regeneration in vessel 30 via control valve 29. The outlet means 28 may include a steam stripping section, not shown, in which useful hydrocarbons are removed from the catalyst prior to regeneration of the catalyst. The partially deactivated catalyst is oxidatively regenerated by controlled contact with air or other regeneration gas at elevated temperature in a fluidized regeneration zone 30 to remove carbonaceous deposits and restore catalyst activity. The catalyst particles are entrained in a lift gas provided via line 47 and transported via riser tube 32 to a top portion of vessel 30. Air is distributed at the bottom of the bed via line 44 to effect fluidization, with oxidation byproducts being carried out of the regeneration zone through cyclone separator 34, which returns any entrained solids to the bed. Flue gas is withdrawn via top conduit 36 for disposal; however, a portion of the flue gas may be recirculated via heat exchanger 38, separator 40, and compressor 42 for return to the vessel through line 47 with fresh oxidation gas fed via line 44 and as fluidizing gas for the regenerator 30 and as lift gas for the catalyst in riser 32.

Regenerated catalyst is passed to the main reactor 20 through conduit 46 provided with flow control valve 48. The regenerated catalyst may be lifted to the catalyst bed through return riser conduit 50 with pressurized olefin feed gas fed through line 14 to catalyst return riser conduit 50. Since the amount of regenerated catalyst passed to the reactor is relatively small, the temperature of the regenerated catalyst does not upset the temperature constraints of the rector operations in significant amount. A series of sequentially connected cyclone separators 52, 54 are provided with diplegs 52A, 54A to return any entrained catalyst fines to the lower bed. These separators are positioned in an upper portion of the reactor vessel comprising dispersed catalyst phase. Filters, such as sintered metal plate filters, can be used alone or in conjunction with cyclones.

The hydrocarbon product effluent separated from catalyst particles in the cyclone separating system is then withdrawn from the reactor vessel 20 through top gas outlet means 56.

The recovered hydrocarbon product comprising $C_5+$ olefins, aromatics, paraffins, alkyl aromatics and naphthenes is thereafter processed as required to provide the desired gasoline product.

Under optimized process conditions the tubulent bed has a superficial vapor velocity of about 0.3 to 2 meters per second (m/sec). At higher velocities entrainment of fine particles may become excessive and beyond about 3 m/sec the entire bed may be transported out of the reaction zone. At lower velocities, the formation of large bubbles or gas voids can be detrimental to conversion. Even fine particles cannot be maintained effectively in a turbulent bed below about 0.1 m/sec.

A convenient measure of turbulent fluidization is the bed density. A typical tubulent bond has an operating density of about 100 to 500 kg/m$^3$, preferably about 300 to 500 kg/m$^3$, measured at the bottom of the reaction zone, becoming less dense toward the top of the reaction zone, due to pressure drop and particle size differentiation. This density is generally between the catalyst concentration employed in dense beds and the dispersed transport systems. Pressure differential between two vertically spaced points in the reactor column can be measured to obtain the average bed density at such portion of the reaction zone. For instance, in a fluidized bed system employing ZSM-5 particles having an apparent packed density of 750 kg/m$^3$ and real density of 2430 kg/m$^3$, an average fluidized bed density of about 300 to 500 kg/m$^3$ is satisfactory.

By virtue of the tubulence experienced in the turbulent regime, gas-solid contact in the catalytic reactor is improved, providing substantially complete conversion, enhanced selectivity and temperature uniformity. One main advantage of this technique is the inherent control of bubble size and characteristic bubble lifetime. Bubbles of the gaseous reaction mixture are small, random and short-lived, thus resulting in good contact between the gaseous reactants and the solid catalyst particles.

A sigificant difference between the process of this invention and conversion processes of the prior art is that operation in the turbulent fluidization regime is optimized to produce high octane $C_5^+$ aliphatic hydrocarbon liquid in good yield from the $C_4^-$ fuel gas feed and to produce high octane $C_7$ to $C_{11}$ aromatic hydrocarbon product in good yield from the catalytic reformate feed. The zeolite catalyst process conditions, including temperature and pressure, in the turbulent regime of the fluidized bed are closely controlled to minimize cracking of $C_3$ to $C_6$ paraffin hydrocarbons in the feed and is an important feature of the present invention. The weight hourly space velocity and uniform contact provides a close control of contact time between vapor or vapor and liquid and solid phases, typically about 3 to 25 seconds. Another advantage of operating in such a mode is the control of bubble size and life span, thus avoiding large scale gas by-passing in the reactor.

As the superficial gas velocity is increased in the dense bed, eventually slugging conditions occur and with a further increase in the superficial gas velocity the slug flow breaks down into a turbulent regime. The transition velocity at which this tubulent regime occurs appears to decrease with particle size. The turbulent regime extends from the transition velocity to the so-called transport velocity, as described by Avidan et al in U.S. Pat. No. 4,547,616, incorporated herein by reference. As the transport velocity is approached, there is a sharp increase in the rate of particle carryover, and in the absence of solid recycle, the bed could empty quickly.

Several useful parameters contribute to fluidization in the turbulent regime in accordance with the process of the present invention. When employing a ZSM-5 type zeolite catalyst in fine powder form such a catalyst should comprise the zeolite suitably bound or impregnated on a suitable support with a solid density (weight of a representative individual particle divided by its apparent "outside" volume) in the range from 0.6-2 g/cc, preferably 0.9-1.6 g/cc. The catalyst particles can be in a wide range of particle sizes up to about 250 microns, with an average particle size between about 20 and 100 microns, preferably in the range of 10-150 microns and with the average particle size between 40 and 80 microns. When these solid particles are placed in a fluidized bed where the superficial fluid velocity is 0.3-2 m/sec, operation in the turbulent regime is obtained. The velocity specified here is for an operation at a total reactor pressure of about 0 to 30 psig (100 to 300 kPa). Those skilled in the art will appreciate that at higher pressures, a lower gas velocity may be employed to ensure operation in the turbulent fluidization regime.

The reactor can assume any technically feasible configuration, but several important criteria should be considered. The bed of catalyst in the reactor can be at least about 5-20 meters in height. Fine particles may be included in the bed, especially due to attrition, and the fines may be entrained in the product gas stream. A typical turbulent bed may have a catalyst carryover rate up to about 1.5 times the reaction zone inventory per hour. If the fraction of fines becomes large, a portion of the carryover can be removed from the system and replaced by larger particles. It is feasible to have a fine particle separator, such as a cyclone and/or filter means, disposed within or outside the reactor shell to recover catalyst carryover and return this fraction continuously to the bottom of the reaction zone for recirculation at a rate of about one catalyst inventory per hour. Optionally, fine particles carried from the reactor vessel entrained with effluent gas can be recovered by a high operating temperature sintered metal filter.

This process can be used with process streams which contains sufficient amounts of light olefins and $C_6$ to $C_8$ aromatics. For example, it can be used to process FCC by-product fuel gas, which typically contains about 10 to 40 wt.% total ethene and propene and catalytic reformate which contains about 2 to 40 wt.% $C_6$ to $C_8$ aromatics.

Reactor Operation

A typical reactor unit employs a temperature-controlled catalyst zone with indirect heat exchange and/or adjustable gas quench, whereby the reaction temperature can be carefully controlled within an operating range of about 500° to 800° F. (204° to 427° C.), preferably at average reactor temperature of 600° to 750° F. (316° to 399° C.).

The reaction temperature can be in part controlled by exchanging hot reactor effluent with feedstock and/or recycle streams. Optional heat exchangers may recover heat from the effluent stream prior to fractionation. Part or all of the reaction heat can be removed from the reactor by using cold feed, whereby reactor temperature can be controlled by adjusting feed temperature. The reactor is operated at moderate pressure of about 50 to 500 psig (445 to 3550 kPa), preferably 100 to 250 psig (790 to 1825 kPa).

The weight hourly space velocity (WHSV), based on olefins in the fresh feedstock is about 0.1-5 WHSV and the weight hourly space velocity (WHSV) based on $C_6$-$C_8$ aromatics 0.01 to 6.0 WHSV.

Typical product fractionation systems that can be used are described in U.S. Pat. No. 4,456,779 and U.S. Pat. No. 4,504,693 (Owen et al).

The present invention is exemplified by the following Example. The process was carried out in a turbulent fluidized bed reactor using a HZSM-5 catalyst comprising a weight ratio of catalyst to silica-alumina binder of 25/75.

EXAMPLE 1

The process is carried out in a fluidized bed reactor using an HZSM-5 zeolite catalyst having an acid value of 40. The reactor bed temperature is maintained at about 600° F. (316° C.) and at a pressure of about 100 psig (790 kPa). The olefin feed is fed at a WHSV of about 0.5, based on ethene and propene. The reformate is fed at a WHSV of about 0.8, based on $C_6$ to $C_8$ aromatics (0.1 based on benzene) in the reformate feed. The reaction is carried out without recycle of light olefins.

The components of the olefin gas feed stream and of the reformate feed stream and the components of the total hydrocarbon feed as well as the components of the hydrocarbon product are given below.

| Individual Feed Stream Compositions | | |
|---|---|---|
| Olefin Gas Wt. % | | |
| Hydrogen | 2.5 | |
| Ethene | 15 | |
| Propene | 15 | |
| Reformate Wt. % | | |
| Benzene | 5 | |
| Toluene | 15 | |
| $C_8$ aromatics | 20 | |
| Olefins | 0 | |
| Total Hydrocarbon Distribution And Yield, Wt. % | Feed | Product |
| Methane | 0 | 0 |
| Ethene | 10 | 1.0 |
| Ethane | 0 | 0 |
| Propene | 10 | 0.5 |
| Propane | 0 | 0.5 |
| Isobutane | 0 | 1.6 |
| n-Butane | 0 | 4.0 |
| Butenes | 0 | 4.5 |
| $C_5{}^+$ Paraffinic Hydrocarbons | 26 | 24 |
| $C_5{}^+$ Olefinic Hydrocarbons | 0 | 7.6 |
| Aromatics Hydrocarbons | | |
| Benzene | 4 | 3.3 |
| Toluene | 12 | 9.7 |
| $C_8$ Aromatics | 16 | 14.8 |
| $C_9{}^+$ Aromatics | 22 | 28.5 |
| Product Properties | | |
| R + O Octane | 95.2 | 97.7 |
| Specific Gravity | .775 | .778 |

The above Examples indicates substantial conversion of $C_2$ and $C_3$ olefins to $C_5{}^+$ olefins and substantial conversion of $C_6$–$C_8$ aromatic hydrocarbons to $C_9{}^+$ aromatic hydrocarbons.

The maximum yield $C_5{}^+$ plus hydrocarbons and alkyl aromatics can be achieved at a conversion temperature between 600°–750° F. (316° to 399° C.). The flexibility of the turbulent regime fluid bed for controlling the reactor temperature under exothermic reaction conditions allows an easy adjustment for achieving the optimal yield structure. The proposed fuel gas-catalytic reformate conversion unit can fit into an existing FCC gas and catalytic reforming plant refinery.

The use of a fluid bed (turbulent zone) reactor in this process offers several advantages over a fixed bed reactor. Due to continuous catalyst regeneration, fluid bed reactor operation will not be adversely affected by oxygenate, sulfur and/or nitrogen containing contaminants presented in FCC fuel gas.

The reaction temperature can be controlled by adjusting the feed temperature so that the enthalphy change balances the heat of reaction. The feed temperature can be adjusted by a feed preheater, heat exchange between the feed and the product, or a combination of both. Once the feed and product compositions are determined using, for example, an on-line gas chromatography, the feed temperature needed to maintain the desired reactor temperature, and consequent olefin and $C_6$ to $C_8$ aromatic conversion, can be easily calculated from a heat balance of the system. In a commercial unit this can be done automatically by state-of-the-art control techniques.

While the invention has been shown by describing preferred embodiments of the process, there is no intent to limit the inventive concept, except as set forth in the following claims.

What is claimed is:

1. A fluidized bed catalytic process for conversion of $C_4{}^-$ light olefinic gas feedstock to $C_5{}^+$ hydrocarbons and for conversion of $C_6$ to $C_8$ aromatic feedstock to $C_7$ to $C_{11}$ aromatics comprising the steps of maintaining a fluidized bed of zeolite catalyst particles in a turbulent reactor bed at a temperature of about 500° to 800° F., said catalyst having an apparent particle density of about 0.9 to 1.6 g/cm$^3$ and a size range of about 1 to 150 microns, an average catalyst particle size of about 20 to 100 microns containing about 10 to 25 weight percent of fine particles having a particle size less than 32 microns;

contacting said feedstocks and passing said feedstocks upwardly through the fluidized catalyst bed under turbulent flow conditions at reaction conditions sufficient to convert at least about 70% of the olefin feedstock and to convert at least 5% of the $C_6$ to $C_8$ aromatic feedstock;

maintaining turbulent fluidized bed conditions through the reactor bed between transition velocity and transport velocity at a superficial fluid velocity of about 0.3 to 2 meters per second; and recovering hydrocarbon product containing $C_5{}^+$ hydrocarbons and $C_7$ to $C_{11}$ aromatic hydrocarbons.

2. A fluidized bed process according to claim 1 wherein the fluidized bed density is about 100 to 500 kg/m$^3$, measured at the bottom of the bed, and wherein the catalyst comprises a siliceous metallosilicate acid zeolite having the structure of ZSM-5 zeolite.

3. The process of claim 1 wherein the feedstocks comprise $C_4{}^-$ light cracking gas comprising about 8 to 50 wt.% ethene and catalytic reformate comprising about 10 to 95 wt.% $C_6$ to $C_8$ aromatics.

4. A process for continuous conversion of $C_4{}^-$ light olefinic gas feedstock and catalytic reformate containing $C_6$ to $C_8$ aromatic hydrocarbons feedstock to heavier hydrocarbon products wherein the feedstocks are contacted together at elevated temperature with a fluidized bed of zeolite catalyst under conversion conditions, which comprises maintaining the fluidized catalyst bed in a vertical reactor column having a turbulent reaction zone by passing feedstock gas upwardly through the reaction zone at a velocity greater than dense bed transition velocity to a turbulent regime and less than transport velocity for the average catalyst particle; and withdrawing a portion of coked catalyst from the reaction zone, oxidatively regenerating the withdrawn catalyst and returning regenerated catalyst to the reaction zone at a rate to control catalyst activity whereby the $C_4{}^-$ light olefins are converted to $C_5{}^+$ olefinic hydrocarbons and the $C_6$ to $C_8$ aromatic hydrocarbons in the catalytic reformate feedstock are converted to $C_7$ to $C_{11}$ aromatic hydrocarbons.

5. The process of claim 4 wherein the superficial feedstock vapor velocity is about 0.3–2 m/sec; the reaction temperature is about 600° to 750° F.; the weight hourly feedstock space velocity (based on olefin equivalent and total reactor catalyst inventory) is about 0.1 to 5 and the weight hourly feedstock space velocity (based on $C_6$ to $C_8$ aromatics equivalent and total reactor catalyst inventor) is about 0.01 to 6.0; and the average fluidized bed density measured at the reaction zone bottom is about 300 to 500 kg/m$^3$.

6. The process of claim 4 wherein the catalyst consists essentially of a medium pore pentasil zeolite having an apparent alpha value of about 1 to 80, and average particle size of about 20 to 100 microns, the reactor catalyst inventory includes at least 10 weight percent fine particles having a particle size less than 32 microns.

7. The process of claim 6 wherein the catalyst particles comprise about 5 to 95 weight percent ZSM-5 zeolite having a crystal size of about 0.02–2 microns.

8. The process of claim 4 wherein said feedstocks comprise $C_4^-$ light olefin hydrocarbons cracking gas containing 5 to 80 wt.% ethene and propene and catalytic reformate hydrocarbons containing 10 to 95 wt.% $C_6$ to $C_8$ aromatics.

9. The process of claim 4 wherein the olefinic feed contains 5 to 60 wt.% ethene and propene and the reformate feed contains 15 to 95 wt.% $C_6$ to $C_8$ aromatics.

10. The process of claim 4 wherein $C_4^-$ hydrocarbon product is separated from the $C_5^+$ hydrocarbon product and is recycled back to the reactor.

11. The process of claim 4 wherein the heat of reaction removal and reactor temperature control are enhanced by controlling feed temperature by heat exchange with olefin gas feed and catalytic reformate feed.

12. A fluidized bed process according to claim 1 wherein the fluidized bed density is about 100 to 500 kg/m$^3$ measured at the bottom of the bed.

13. A fluidized bed process according to claims 1 or 4 integrated with a petroleum refinery unsaturated gas separation process and catalytic reforming process said integrated process obtaining light olefin containing feed from a FCC unit and catalytic reformate feed from a reformer unit.

* * * * *